United States Patent
Patrick

(10) Patent No.: US 6,620,836 B1
(45) Date of Patent: Sep. 16, 2003

(54) ANTIARRHYTHMIC AND TRANQUILIZER COMPOSITION AND TREATMENT

(76) Inventor: Jay Patrick, 19631 Pauling, Foothill Ranch, CA (US) 92610

(*) Notice: Subject to any disclaimer, the term of this patent is extended or adjusted under 35 U.S.C. 154(b) by 1161 days.

(21) Appl. No.: 09/002,342

(22) Filed: Jan. 2, 1998

Related U.S. Application Data

(63) Continuation-in-part of application No. 08/786,861, filed on Jan. 22, 1997, now abandoned.

(51) Int. Cl.$^7$ ............... A61K 31/405; A61K 31/40; A61K 31/19
(52) U.S. Cl. ............... 514/419; 514/415; 514/574; 514/821
(58) Field of Search ............... 514/415, 419, 514/574, 821

(56) References Cited

U.S. PATENT DOCUMENTS

| | | | |
|---|---|---|---|
| 4,600,723 A | * 7/1986 | Short et al. | 514/416 |
| 4,855,305 A | * 8/1989 | Cohen | 514/171 |
| 5,700,828 A | * 12/1997 | Federowicz et al. | 514/419 |

OTHER PUBLICATIONS

Berge, S. M. et al., Journal of Pharmaceutical Sciences, vol. 66, No. 1, pp. 1–19 (Jan. 1977).*
Morton, D.J., Journal of Pineal Research, vol. 6, pp. 141–147 (1989).*
Wynn, V.T. et al., Journal of Pineal Research, vol. 5, pp. 427–435 (1988).*
DiPiro, J.T. et al., Pharmacotherapy: A Pathophysiologic Approach, New York: Elsevier, 1989, pp. 150–155 and 166–167.*
Goodman Gilman et al., The Pharmacological Basis of Therapeutics (6th Ed.), New York: MacMillan, pp. 880–881, 1980.*
Budavari et al., The Merck Index (11th Ed.), Rahway, NJ:Merck & Co., Inc., 1989, pp. 891–894.*
HCAPLUS abstract, AN 1990:62488, Popovici et al., 1989.*

* cited by examiner

Primary Examiner—Theodore J. Criares
(74) Attorney, Agent, or Firm—Charles H. Thomas

(57) ABSTRACT

A composition employing a small amount of the hormone melatonin combined with a magnesium compound is formed into a lozenge or into a timed release tablet to act as an antiarrhythmic agent. As a lozenge to be dissolved in the mouth, it may incorporate magnesium in several forms such as a citrate, as a niacinate, as an aspartate, or as an orotate. The preferred formulations according to the invention alleviate cardiac arrhythmia, as well as the extreme manifestation of this condition known as atrial fibrillation. Magnesium citrate is not only beneficial to the heart muscle but also contributes to a laxative effect that counters the constipating action of the melatonin. As a time release tablet for daytime use, the same ingredients indicated above may be combined in tablet or capsular form, but are accompanied by the addition of agents which stimulate the mind such as tyrosine and phenylalanine. These stimulants serve to counter the sleep-inducing action of the melatonin. The timed release forms of the composition may also be formulated as a tranquilizer or to reduce mental anxiety.

6 Claims, No Drawings

ANTIARRHYTHMIC AND TRANQUILIZER COMPOSITION AND TREATMENT

The present invention is a continuation-in-part of U.S. application Ser. No. 08/786,861, filed Jan. 22, 1997, now abandoned.

BACKGROUND OF THE INVENTION

1. Field of the Invention

The present invention relates to a composition and method of treatment of cardiac arrhythmia.

2. Description of the Prior Art

A cardiac condition which has long puzzled heart specialists is atrial fibrillation, which is abbreviated herein and in the medical profession as AF. The condition of AF can be described as an irregular and very rapid heart beat. In extreme cases it may result in sudden death.

AF is an extreme form of cardiac arrhythmia. Cardiac arrhythmia is the condition in a subject of an irregular heart beat. The heart of a subject having a condition of cardiac arrhythmia departs from the normal, rhythmic pulsing produced by the contraction and relaxation of the heart muscles, and instead pulses in an erratic manner. Indeed, in an arrhythmic subject the heart may pause for as long as several seconds, neither contracting nor relaxing. Such a pause is typically followed by a few very rapid heartbeats.

Persons considered to be medically normal and healthy may experience cardiac arrhythmia, especially during stress or exercise. Cardiac arrhythmia is also typical in cases of acute alcoholism and after surgery. However, although cardiac arrhythmia may be tolerated by a subject for many years, the condition of cardiac arrhythmia usually precedes or is a contributing factor to AF which is a much more dangerous condition. Persistent AF usually occurs in patients with rheumatic heart disease, microvalve disease, hypertension, or thyroidtoxicosis (Taber's Cyclopedic Medical Dictionary). Regarding treatment, Tabor's advises that the patient should be instructed concerning optimum physical function by utilizing frequent rest periods and the need to restrict sodium intake, and also instructed concerning drugs that are prescribed.

A widespread view among many physicians is that body functions, including cardiac arrhythmia, should be controlled through the use of drugs. Such drugs have been administered under the mistaken view that they prevent cardiac arrest and death. As disclosed in the recent book *Deadly Medicine* by Thomas J. Moore, Simon & Schuster, the administration of drugs intended to treat cardiac arrhythmia is thought to have induced the premature death, in just a few years, of an estimated 50,000 people. Such drugs continue to be administered despite a definitive medical experiment, as reported by Moore and financed by the U.S. Government, that has proven that such drugs do not prevent cardiac arrest, but in fact cause it. As stated by Moore, the effect of these drugs was so sudden and unexpected that people literally dropped dead while going about their normal lives. According to him, "The result of the single medical misjudgment about the proper use of these drugs has produced a death toll larger than the United States combat losses in wars such as Korea and Viet Nam."

SUMMARY OF THE INVENTION

The present invention is a composition and method of treatment of cardiac arrhythmia which avoids the use of conventional drugs, but instead relies upon a composition, one of the principal active components of which is generated in the human body itself. This component is the natural hormone melatonin.

Melatonin is a hormone produced by the pineal gland of the body. The production of melatonin is induced by the perception of darkness as transmitted from the eyes to the pineal gland between the two hemispheres of the brain. The pineal gland of a normal person produces approximately 500 mcg (micrograms) of melatonin daily. However, starting at age 12, or even earlier, production of this key hormone goes into steady decline. In an octogenarian the amount of melatonin produced is quite nominal. Whereas at one time the pituitary gland was thought of as being the master gland of the body, it is now becoming increasingly evident that the pineal gland is truly the master gland, and that the decline in the output of melatonin is clearly an aspect of aging. Melatonin is known to be a sleep inducing substance. Indeed, melatonin is sold commercially in sublingual and in tablet form in which each tablet contains about 2.5 mg to 5.0 mg of melatonin as a treatment for insomnia.

The powerful drugs with possibly dangerous, even fatal side effects that are conventionally used for the treatment of cardiac arrhythmia can be replaced with a composition according to my invention. This composition includes melatonin potentiated with compounds of magnesium and preferably including the mineral ascorbates of calcium, magnesium, and zinc. By using my composition conventional antiarrhythmic drugs can be replaced entirely in the treatment of cardiac arrhythmia.

I have discovered that melatonin, when taken in suitable form and at a relatively low strength, in combination with any one or more of a number of different compounds of magnesium, substantially reduces cardiac arrhythmia. This is especially true when the hormone is taken in sublingual form at a low level, preferably at strength of between about 25 micrograms and about 10 milligrams.

I have further discovered that although melatonin by itself is beneficial and useful for treating cardiac arrhythmia, it is much more effective when combined with other substances. Specifically, I have found that the combination of melatonin at a strength of between about 25 micrograms and 10 milligrams, in combination with a magnesium compound, administered sublingually, is extremely beneficial in treating cardiac arrhythmia. Preferably the magnesium is combined with melatonin in the form of calcium magnesium ascorbate, magnesium citrate, magnesium niacinate, or a combination of these magnesium compounds. Other magnesium compounds, such as magnesium aspartate or magnesium orotate may be used in addition or as substitutes.

The combination of magnesium with melatonin has several effects which are not readily apparent. Calcium and magnesium are essential to the function of the heart. The heart muscle cannot contract without calcium, and cannot relax without magnesium.

In the conventional treatment of heart disease, which is often characterized or accompanied by cardiac arrhythmia, calcium channel blockers have gained wide-spread use. However, when persons take such drugs the calcium in their systems is not adequately-opposed by the muscle relaxing magnesium. I regard this as a backward approach, in that more should be done to increase the magnesium which is essential to the relaxation of the heart muscle, rather than to cut down on the action of the calcium. The action of these electrolytes must be well balanced for the heart to function normally for many years of service.

Rather than using calcium channel blockers to hold off the sometimes frenzied action of calcium, I believe that the combination of magnesium with melatonin has a synergistic effect in the relaxation of the heart muscle. Indeed, this action is so positive that users have reported that the modulating effect can be felt within minutes after the product is dissolved in the mouth. Thus, a composition containing melatonin in combination with magnesium treats cardiac arrhythmia by promoting the relaxation of the heart muscle through the use of both melatonin and magnesium, as contrasted to the conventional approach of attempting to promote relaxation by reducing the action of calcium on the heart muscle.

The combination of magnesium with melatonin in the form of magnesium citrate also has another beneficial effect which is not readily apparent. It is well established that melatonin slows the digestive process, as noted in the book *Melatonin Miracle*, by Drs. Walter Pierpaoli and William Regelson. Indeed, one of the adverse side effects of the commercially available melatonin sleep inducing tablets that are commercially available is constipation. This is a problem which is well documented in the literature. By augmenting melatonin with magnesium citrate the constipating effect of melatonin is reduced.

A further beneficial substance which is preferably combined with the magnesium and magnesium citrate is vitamin C (calcium magnesium ascorbate). The inclusion of vitamin C in the formulation is beneficial since most people who have heart problems are under stress, and therefore require more vitamin C. Preferably, the antiarrhythmic composition includes vitamin C as calcium magnesium ascorbate to the extent of between about 30 and about 130 mg.

The use of magnesium compounds in combinations with melatonin has other beneficial affects on a human subject in addition to treatment of cardiac arrhythmia. It has now been established that are at least three genetic liver diseases from which humans suffer, unlike most other animals. These diseases are:

(1) Hypoascorbemia, which is the inability to produce the mineral ascorbates of Vitamin C;

(2) Hypouricasemia, which is the inability to produce uricase; and (3) Hypomelatoninemea, which is the nearly total decline in production of the hormone melatonin by the pineal gland that occurs with aging.

While 99.9 percent of all other animals possess the ability to internally produce mineral ascorbates of Vitamin C, human beings do not. The metabolic uses of the mineral ascorbates are almost endless. Mineral ascorbates give major support to the immune system and are essential in the formation of the connective tissue that represents more than thirty percent of the protein of the human body. Mineral ascorbates also perform a multitude of other biochemical actions and reactions. Therefore, the inclusion of magnesium in the form of a mineral ascorbate, such as calcium magnesium ascorbate, is highly desirable to enhance support to the immune system.

While uric acid is an excellent antioxidant which also stimulates brain function, an excess of this substance can bring on gout. Gout is an extremely painful condition that can extend to almost every part of the body, and often manifests itself as a very painful swelling in one or more toes of an individual. The administration of magnesium compounds in combination with melatonin may enhance the body's ability to produce uricase, thus relieving the ailment of gout.

While melatonin is known chiefly for its ability to induce sleep, many researchers have adopted the belief that the decline of the body's production of this hormone, starting at age twelve, is an aging factor. For example, researcher E. Cheraskin of the University of Alabama has commented that the body makes economical use of the substances it produces, and that most of the substances have multiple functions in the body. Thus, it is not surprising to me to find that the administration of melatonin in combination with a magnesium compound to a human subject enhances a sense of well being of the recipient. It is my belief that, when combined with a suitable form of magnesium, melatonin works synergistically to relax the mind and body.

The inclusion of zinc ascorbate in the formulation of my invention is likewise beneficial. Zinc ascorbate is known to work with melatonin in enhancing the immune system. However, since the body can be responsive to every specific benefit, it is to be expected that some benefit would accrue to the heart muscle by the inclusion of zinc ascorbate in the formulation.

According to the present invention, an antiarrhythmic composition is provided which includes between about 25 micrograms and about 10 milligrams of melatonin in combination with between about 5 milligrams and about 100 milligrams of a magnesium compound. This substance is preferably administered to a human subject in sublingual tablet form.

The antiarrhythmic composition may also be augmented with other substances. For example, vitamin B6 is preferably included as well to the extent of between about 5 and 15 mg.

I have discovered that the formulation of my invention has several important benefits to human subjects. Primarily, the composition of my invention helps to reduce arrhythmia of the heart. Also, in certain formulations, it aids in inducing sleep. Other formulations can be employed to render the composition effective as a tranquilizer, as well as an antiarrhythmic treatment substance.

A further benefit of the preferred formulation of my composition is that it has a calming effect on the mind. The amino acids present in the preferred formulation of the composition tend to aid in maintaining mental alertness. Nevertheless, the formulation as a whole can act as a tranquilizer.

The antiarrhythmic treatment composition of the invention may be administered both as a lozenge and as a timed release tablet. When administered as a lozenge the composition can be dissolved in the mouth at bedtime and goes quickly into circulation. This aids in inducing sleep. On the other hand, a timed release tablet may be formulated so as to avoid the sedative effect of melatonin during normal daytime activities.

When formulated as a timed release tablet, the antiarrhythmic composition of the invention has two beneficial side effects. It lowers the amount of melatonin affecting the senses at any given time, so as not to induce sedation during the day. Additionally, it extends the benefit of the product for treatment of cardiac arrhythmia for some eight to twelve hours. A timed release form of the composition is highly desirable so as to allow administration of a tiny amount of melatonin during the daytime which is sufficient to achieve an antiarrhythmic effect, but not enough to induce drowsiness.

Of course the formulation can be tailored by the inclusion or omission of the other substances suggested herein to derive the benefits that they contribute.

In one broad aspect the present invention may be considered to be a composition comprising between about 25 micrograms and about 10 milligrams melatonin and between about 5 milligrams and 100 milligrams of at least one magnesiu m compound. The magnesium compound, or plurality of compounds, is preferably selected from the group consisting of magnesium citrate, calcium magnesium ascorbate, magnesium niacinate, magnesium aspartate, and magnesium orotate. When magnesium citrate is employed in the formulation, it is preferably included in an amount of between about 25 and about 50 milligrams. When magnesium aspartate or magnesium orotate are employed, these compounds are preferably included to the extent of between about 26 and about 50 milligrams. When magnesium niacinate is utilized in the formulation, it is preferably present to the extent of between about 5 and 20 milligrams. Any one or more of these different magnesium compounds may be employed as a substitute, or in addition to any other magnesium compounds so as to enhance the beneficial effects of the different magnesium compounds described herein.

In another broad aspect the invention may be considered to be an improvement in a medicinal dosage for administration to a human patient that includes between about 25 micrograms and about 10 milligrams of melatonin. The improvement of the invention resides in the augmentation of the melatonin with between about 5 and about 100 milligrams of a compound of magnesium, preferably one or more of those hereinbefore suggested.

In a further broad aspect the invention may be considered to be a method of treating a human patient for cardiac arrhythmia comprising administering to the patient a composition comprising between about 25 micrograms and about 10 milligrams of melatonin and between about 5 milligrams and about 100 milligrams of at least one compound of magnesium. The formulation preferably includes zinc ascorbate as well, since zinc ascorbate is known to work well with melatonin in enhancing the immune system of the body.

The composition and treatment of cardiac arrhythmia according to the invention may be further described with reference to the following examples.

EXAMPLE 1

The following substances are mixed together so as to form a lozenge:

| | |
|---|---|
| Melatonin | 0.5 mg |
| Magnesium Citrate | 25 mg |
| Vitamin B6 | 10 mg |
| Zinc Ascorbate | 5 mg |
| Plus Excipients | |

The excipients are conventional substances used to give the mixture bulk so as to allow it to be formed into a lozenge. For example, dibasic calcium phosphate may be used as an excipient in the formulation of this Example.

A subject who is known to have a condition of cardiac arrhythmia places a lozenge having the foregoing formulation beneath the tongue at bedtime and moves the lozenge about beneath the tongue, so as to absorb it directly into the circulatory system. The lozenge will not only reduce cardiac arrhythmia, but induce a good, peaceful sleep. One subject who has been subject to atrial fibrillation reported that ten to fifteen minutes after taking the lozenge form of melatonin in the formulation set forth above, his fibrillation halted. Another case reported is that of an individual who, if he slept on his right side, prior to treatment according to the invention, experienced great thumping of the heart. This no longer occurs since he has been taking a melatonin lozenge of the composition set forth above each night before going to sleep.

EXAMPLE 2

The formulation and administration of the lozenge of Example 1 are repeated with the exception that 80 milligrams of Vitamin C as calcium magnesium ascorbate are added to the substances which are mixed together so as to form a lozenge.

EXAMPLE 3

The formulation and administration of the lozenge of Example 1 are repeated with the exception that the amount of magnesium citrate is increased to 40 milligrams.

EXAMPLE 4

The formulation and administration of the lozenge of Example 3 are repeated with the exception that magnesium aspartate is substituted for magnesium citrate.

EXAMPLE 5

The formulation and administration of the lozenge of Example 3 are repeated with the exception that magnesium orotate is substituted for magnesium citrate.

EXAMPLE 6

The formulation and administration of the lozenge of Example 1 is repeated with the exception that 15 milligrams of magnesium niacinate are substituted for the magnesium citrate.

EXAMPLE 7

A composition according to the invention may be formulated in a time-release form for day-time use as an antiarrhythmic agent and also as a mood enhancer. Such a timed-release form of antiarrhythmic composition is provided with the following formulation:

| | |
|---|---|
| Melatonin | 0.25 mg |
| Magnesium Citrate | 25 mg |
| Vitamin B6 | 10 mg |
| Zinc Ascorbate | 10 mg |
| Tyrosine | 25 mg |
| Phenylalanine | 25 mg |

The foregoing mixture is encapsulated in a conventional, timed release medium which is a type of gel, shellac, or glaze that is permeated by digestive fluids over time. For example, methyl cellulose may be used for this purpose.

In this formulation tyrosine and phenylalanine have been added to enhance brain activity to offset the sedative action of the melatonin. A timed release tablet, having the foregoing formulation is administered to a subject each morning. The amount of melatonin in the timed release tablet is small enough so that the subject does not experience drowsiness during the daytime. Nevertheless, it is sufficient to reduce cardiac arrhythmia for a period of eight to twelve hours. While 0.25 milligrams is the preferred amount of melatonin in the time release formulation, the amount of melatonin can be reduced to as low as about 25 micrograms and still produce the beneficial effects described.

EXAMPLE 8

The formulation and administration of the lozenge of Example 7 are repeated with the exception that 80 milligrams of Vitamin C as calcium magnesium ascorbate are added to the substances which are mixed together so as to form a lozenge.

EXAMPLE 9

The formulation and administration of the timed release medium of Example 7 are repeated with the exception that the amount of magnesium citrate is increased to 40 milligrams.

EXAMPLE 10

The formulation and administration of the timed release medium of Example 9 are repeated with the exception that magnesium aspartate is substituted for magnesium citrate.

EXAMPLE 11

The formulation and administration of the timed release medium of Example 9 are repeated with the exception that magnesium orotate is substituted for magnesium citrate.

EXAMPLE 12

The formulation and administration of the timed release medium of Example 7 are repeated wit the exception that 10 milligrams of magnesium niacinate are substituted for the magnesium citrate.

Undoubtedly, numerous variations and modifications in the formulation and treatment according to the invention will become readily apparent to those familiar with treatment of cardiac arrhythmia. Accordingly, the scope of the invention should not be construed as limited to the foregoing examples.

I claim:

1. A method of treating a human patient for cardiac arrhythmia comprising administering to said patient a composition comprising between about 25 micrograms and about 10 milligrams of melatonin and between about 5 milligrams and about 100 milligrams of at least one compound of magnesium.

2. A method according to claim 1 comprising formulating said composition with between about 25 and about 50 milligrams of magnesium citrate.

3. A method according to claim 1 comprising formulating said composition with at least about 5 milligrams magnesium niacinate.

4. A method according to claim 1 wherein said at least one compound of magnesium is selected from the group consisting of magnesium citrate, calcium magnesium ascorbate, magnesium niacinate, magnesium aspartate, and magnesium orotate.

5. A method according to claim 1 further comprising administering said composition sublingually.

6. A method according to claim 1 wherein said composition comprises at least about 30 milligrams of a stimulant selected from the group consisting of tyrosine and phenylalanine and further comprising encapsulating said composition in a timed release medium and administering said composition orally.

* * * * *